United States Patent [19]

Lowe

[11] Patent Number: 5,786,443
[45] Date of Patent: Jul. 28, 1998

[54] PROCESS OF MAKING POLYESTER PREPOLYMER

[75] Inventor: David James Lowe, Wilmington, Del.

[73] Assignee: E. I. du Pont de Nemours and Company, Wilmington, Del.

[21] Appl. No.: 764,370

[22] Filed: Dec. 12, 1996

Related U.S. Application Data

[60] Provisional application No. 60/008,611, Dec. 15, 1995.

[51] Int. Cl.$^6$ .................................................. C08G 63/02
[52] U.S. Cl. .................... 528/272; 528/272; 528/274;
    528/296; 528/298; 528/300; 528/301; 528/302;
    528/307; 528/308; 528/308.6; 528/484;
    528/491; 528/501; 528/503; 526/67; 526/68
[58] Field of Search .................................. 528/272, 274,
    528/296, 298, 300, 301, 302, 307, 308,
    308.6, 484, 491, 501, 503; 526/67, 68

[56] References Cited

U.S. PATENT DOCUMENTS

| | | | |
|---|---|---|---|
| 2,802,028 | 8/1957 | England | 260/539 |
| 3,192,184 | 6/1965 | Brill et al. | 260/75 |
| 3,506,622 | 4/1970 | Higgins | 260/75 |
| 3,551,386 | 12/1970 | Berkav et al. | 260/75 |
| 3,590,072 | 6/1971 | Leybourne, III | 260/475 |
| 3,676,485 | 7/1972 | Lewis et al. | 260/475 P |
| 3,697,579 | 10/1972 | Balint et al. | 260/468 R |
| 3,819,585 | 6/1974 | Funk et al. | 528/305 |
| 3,927,982 | 12/1975 | Chapman et al. | 23/260 |
| 4,097,468 | 6/1978 | James et al. | 526/68 |
| 4,110,316 | 8/1978 | Edging et al. | 526/68 |
| 4,180,635 | 12/1979 | Fischer et al. | 526/68 |
| 4,973,655 | 11/1990 | Pipper et al. | 528/272 |
| 5,064,935 | 11/1991 | Jackson et al. | 528/272 |
| 5,434,239 | 7/1995 | Bhatia | 528/274 |

Primary Examiner—Samuel A. Acquah

[57] ABSTRACT

A continuous process for preparing polyester prepolymer comprising the steps of esterifying a diacid with a diol, reacting the esterified product with additional diol, and passing the product downward through a countercurrent column reactor while inert gas flows upward through the column reactor. The resulting prepolymer product has fewer acid end groups than the esterified material.

23 Claims, 1 Drawing Sheet

PROCESS OF MAKING POLYESTER PREPOLYMER

FIELD OF THE INVENTION

This application claims the priority benefit of U.S. Provisional Application 60/008,611, filed Dec. 15, 1995.

An improved process for making polyester prepolymer involves several steps. In particular, the process comprises an esterification reaction, a diol-incorporation reaction, and a heated countercurrent column reactor. The prepolymer produced by the present process is especially useful for making polymer of higher-molecular-weight polyester product in a finisher or the like.

BACKGROUND OF THE INVENTION

Processes for the continuous preparation of polyester, for example poly(ethylene terephthalate) (hereinafter PET), are disclosed in numerous patents. Poly(ethylene terephthalate) (PET) can be prepared starting with a transesterification reaction in which dimethyl terephthalate (DMT) and a substantial excess of ethylene glycol (EG) are contacted in the presence of a transesterification catalyst. In an esterification process, as compared to a transesterification process, the PET is prepared by reacting terephthalic acid (TPA) and excess EG at slightly above atmospheric pressure to keep out oxygen and at temperatures of about 260° C. to about 300° C. An esterification reaction mass or a transesterification reaction mass, as the case may be, is then typically treated in two or more further reaction stages operating at reduced pressure. These further reaction stages facilitate the removal of reaction products, such as ethylene glycol, and degradation by-products, such as diethylene glycol (DEG), and allow sufficient precondensation and further esterification to form prepolymer suitable for feed to a finisher, that is, a continuous polycondensation reactor.

Continuous processes for direct esterification of TPA with EG are disclosed by Leybourne III in U.S. Pat. No. 3,590,072, by Lewis et al. in U.S. Pat. No. 3,676,485, by Balint et al. in U.S. Pat. No. 3,697,579, and by Chapman et al. in U.S. Pat. No. 3,927,982. The resulting terephthalic ester is subsequently converted to a high-molecular-weight polyester by condensation polymerization under low absolute pressure conditions. Higgins, in U.S. Pat. No. 3,506,622, teaches that ethylene glycol recovered from the polymerization can be used directly in the direct esterification reaction without detrimental effects.

In a conventional, continuous process starting from TPA, the vapors formed during polymerization consist primarily of ethylene glycol, but also contain from about 2 to about 35 weight percent of water vapor. It is economically important to recover the ethylene glycol for reuse. The vapors formed during polymerization can be condensed and recycled, without removing the water, for use in the feed to the direct esterification reaction. A highly efficient process is required, however, for condensing the vapors, since the capacity and the efficiency of vacuum pumping means for maintaining the low pressure used in polymerization depends on the load of uncondensed vapors.

The process disclosed by Edging et al. in U.S. Pat. No. 4,110,316 comprises conducting vapors from a continuous polyester terephthalate polymerizer into a spray condenser. In a first stage, the vapors are sprayed with ethylene glycol liquid containing less than 10 weight percent water to condense the vapors. Vapors from the finisher polymerizer are treated in a similar way in a second stage, and then are passed back into the first stage. Ethylene glycol from the first stage is passed back to the prior esterification reaction.

In U.S. Pat. No. 4,180,635, Fischer et al. disclosed purifying vapors formed during polycondensation in a two-part distillation column. The final vapors have a residual content of organic starting materials of less than 1.5 percent by weight, based on the total weight of the effluent and the unconverted starting materials. The unconverted starting materials are recycled in the process.

Conventional processes for making PET are inherently a source of environmental contamination by virtue of the fact that several stages prior to the final polycondensation (i.e., the precondensation stages) are operated at reduced pressure. This is a problem shared by both continuous and batch processes. The operation of precondensation stages at reduced pressure on a commercial scale generally requires vacuum sources, such as, for example, steam jets or vacuum pumps. When a vacuum source is used, environmental contamination can occur because some of the volatile organics being removed in the precondensation stages cannot be fully condensed. The organic volatiles may then be emitted into the environment from the vacuum source. Accordingly, additional measures are necessary to protect the environment from the volatile organics that may be emitted by the vacuum source.

Jackson et al., in U.S. Pat. No. 5,064,935, disclose an atmospheric process for preparing an oligomer of poly (butylene terephthalate) or an oligomer of poly(butylene isophthalate). The process involves forming a transesterification reaction mass by the reaction of dimethyl terephthalate with butanediol, or the reaction of dimethyl isophthalate (DMI) with butanediol. The transesterification reaction mass is fed into a countercurrent column reactor and flows downward, while simultaneously a heated inert gas flows upward.

Brill et al., in U.S. Pat. No. 3,192,184, disclose a process for continuously producing a prepolymer of bis-2-hydroxy ethyl terephthalate, which process comprises continuously flowing bis-2-hydroxy ethyl terephthalate and/or low-molecular-weight polymers thereof downward over a substantially vertical stationary surface. The surface is provided with protuberances defining symmetrically patterned channels to promote distribution of the liquid as a film. The film is maintained under elevated temperature and reduced pressure to promote polymerization and form a liquid polymer having an intrinsic viscosity not greater than about 0.4, and vaporous by-products are continuously removed.

U.S. Pat. No. 5,434,239 to Bhatia discloses an atmospheric process for the continuous production of polyester wherein a melt of dihydroxy ethyl terephthalate, or its low-molecular-weight oligomer, is intimately contacted with an inert gas to facilitate polymerization and the removal of reaction by-products. Also disclosed is a suitable apparatus consisting of a horizontal, agitated cylindrical vessel.

U.S. Pat. No. 3,551,386 discloses a column reactor for making PET polymer but does not use a diol incorporation reactor.

It would be advantageous to have an efficient process to make poly(ethylene terephthalate) at atmospheric pressure beginning with an esterified reaction mass. Elimination of vacuum systems present an opportunity to reduce investment and avoid oxygen in the process system. Additionally, there still exists a need to reduce the amount of excess EG used and thus reduce the size of EG recycle stress or to improve the utilization of EG, to reduce contamination of the environment with volatile organics, and to improve the efficiency of PET polymerization.

SUMMARY OF THE INVENTION

The present invention is directed to a continuous process for preparing polyester prepolymer in a column reactor which process comprises the steps of:

(a) esterifying a diacid with a diol in an esterification reactor to form an esterified material having a carboxyl content of about 400 to about 1200 meq/kg and a degree of polymerization of about 2 to about 15;

(b) incorporating diol into the esterified material by continuously feeding the esterified material and diol to a diol-incorporation reactor wherein the pressure ranges from about 24.7 psia to 189.7 psia (170 kPa to 1310 kPa) and the temperature ranges from about 200° C. to 350° C. and wherein the diol is fed to the diol-incorporation reactor at a flowrate ranging from 0.5% to 15% of the flowrate of the esterified material, and allowing the diol and esterified material to react for at least 15 seconds in the diol-incorporation reactor to obtain a reaction product having a degree of polymerization ranging from about 2 to about 7 and a carboxyl content of about 10 to about 300 meq/kg lower than the esterified material entering the diol-incorporation reactor;

(c) continuously passing the reaction product through a heated, pressure-reducing device, thereby allowing some of the diol and other volatile reaction products to flash off;

(d) continuously passing the reaction product into a top portion of a heated countercurrent column reactor containing about 2 to 50 plates, while countercurrently passing into a bottom portion of the same column reactor a stream of predominantly inert gas at a flowrate of about 0.02 to about 0.75 (g inert gas)/(kg bottoms product), wherein the minimum temperature of the inert gas, at it enters the column reactor should be at least 5° C. above the freezing point, defined in ASTM D 3418-82, where it is referred to as the peak crystallization temperature, of the resulting prepolymer recovered from the bottom of the countercurrent column reactor and the flowrate of the reaction product is such that it has a residence time in the column reactor of at least about 2 minutes;

(e) withdrawing a gas stream from the top of the column reactor and removing water, diol, low-molecular-weight solids and degradation reaction products from the gas stream;

(f) collecting, from the bottom of the column reactor, polyester prepolymer having a lower carboxyl content and higher degree of polymerization than the esterified material from the esterification reactor, whereby the carboxyl content is in the range of about 25 to about 800 meq/kg lower than the esterified material entering the diol-incorporation reactor and the degree of polymerization is in the range of about 10 to about 30.

The diacid is selected from aliphatic or aromatic diacids having a molecular weight less than 300, such as terephthalic acid, isophthalic acid, adipic acid succinic acid and naphthalenedicarboxylic acid. The diol is selected from aliphatic and cycloaliphatic diols having a molecular weight less than 400 such as ethanediol, propanediol, butanediol, and dimethylolcyclohexane.

A preferred embodiment of the process is used for preparing poly(ethylene terephthalate) prepolymer and comprises (a) esterifying terephthalic acid with ethylene glycol in an esterification reactor to form an esterified material having a carboxyl content of about 400 to about 1200 meq/kg and a degree of polymerization of about 2 to about 15;

(b) incorporating glycol into the esterified material by continuously feeding the esterified material to a glycol-incorporation reactor wherein the pressure ranges from about 24.7 psia to 189.7 psia (170 kPa to 1310 kPa) and the temperature ranges from about 200° C. to about 350° C. and wherein the ethylene glycol is fed to the glycol-incorporation reactor at a flowrate ranging from about 0.5% to about 15% of the flowrate of the esterified material, and allowing the ethylene glycol and esterified material to react for at least 15 seconds in the glycol-incorporation reactor to obtain a reaction product having a degree of polymerization ranging from about 2 to about 7 and a carboxyl content of about 25 to about 300 meq/kg lower than the esterified material entering the glycol-incorporation reactor;

(c) continuously passing the reaction product through a heated, pressure-reducing device, thereby allowing ethylene glycol and other volatile condensation products to flash off;

(d) continuously passing the reaction product into a top portion of a column reactor containing about 2 to about 50 plates, while countercurrently and continuously feeding into a bottom portion of the column reactor a stream of predominantly inert gas at a flowrate of about 0.02 to about 0.75 (kg inert gas)/(kg bottoms product), wherein the minimum temperature of the inert gas as it enters the column reactor is greater than about 255° C. and the flowrate of the reaction product is such that it has a residence time in the column reactor of at least about 2 minutes;

(e) withdrawing a gas stream from the top of the column reactor and removing water, ethylene glycol, low-molecular-weight solids and degradation reaction products from the gas stream;

(f) collecting, from the bottom of the column reactor, poly(ethylene terephthalate) having a lower carboxyl content and a higher degree of polymerization than the esterified material from the esterification reaction, whereby the carboxyl content is in the range of about 25 to about 800 meq/kg lower than the esterified material entering the glycol-incorporation reactor and the degree of polymerization is in the range of about 10 to about 30.

It is to be understood that the foregoing general descriptions and the following detailed description are exemplary and explanatory only and are not restrictive of the invention as claimed.

DETAILED DESCRIPTION OF THE INVENTION

Figure 1:
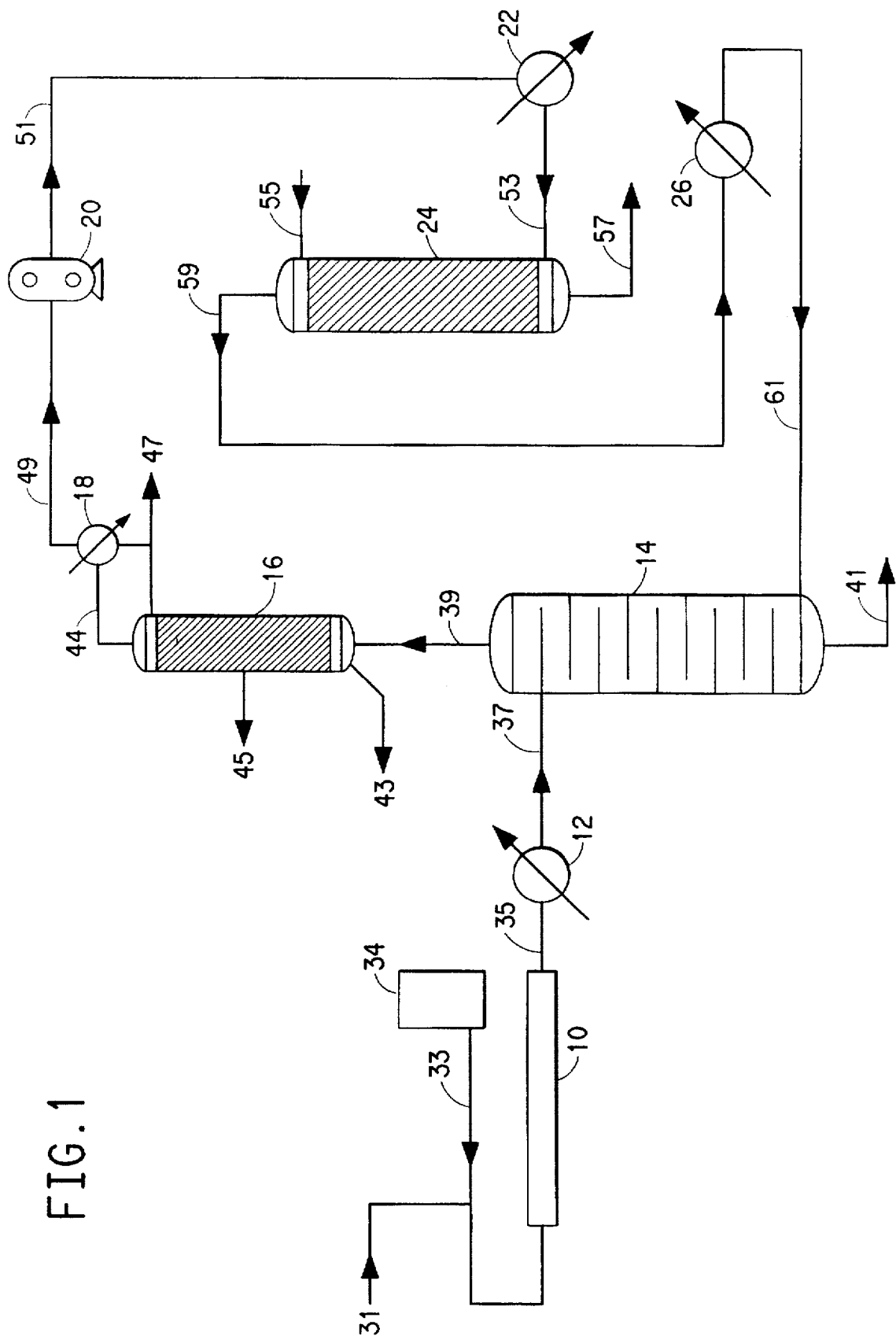
FIG. 1 is a diagrammatic flow sheet for a process according to the present invention.

The present process makes use of a continuous countercurrent column reactor to convert esterified material from an esterification-reaction stage into a polyester prepolymer. This prepolymer is useful as a feed material for one or more subsequent polycondensation stages. The stages or steps of the present process are described in detail below.

1. Esterification Reaction Stage

The process begins by reacting diacid with diol to form an esterified material. Such esterification is described in U.S. Pat. No. 3,927,982, which is incorporated herein by reference. This esterification may be carried out with or without an esterification catalyst. The esterified material should exhibit a degree of polymerization (DP) in the range of about 2 to about 15, and a carboxyl ends content in the range of about 400 to 1200 meq/kg. The esterified material should have a minimum discharge temperature of at least 5° C. above the freezing point of the esterified material.

The definition for the "degree of polymerization" (DP) is the average number of repeat units in a polymer chain and, therefore, may not necessarily be an integer.

The DP of PET, for example, can be determined by gel permeation chromatography using appropriate PET standards.

The DP is one way of expressing the molecular weight of the polyester. Another comparable measure of molecular weight is the inherent viscosity (I) of the polymer.

By the term "oligomer" is meant a low-molecular-weight polymer, for example, a polymer having a degree of polymerization (DP) in the range of about 2 to about 10.

By the term "prepolymer" is meant a low molecular weight polymer having a degree of polymerization between about 10 and 30.

By the term "carboxyl content" or "acid end-group content" is meant the quantity of acid end groups per unit mass, usually expressed in milliequivalents of acid per kg of polymer. Carboxyl content is determined by the following method. A polymer sample is weighed in a 100 ml beaker that contains a Teflon® coated stirring bar. Fifty ml of o-cresol is added to the beaker and stirred while the beaker is heated on a hot plate to a temperature of about 120° to 140° C. until all the polymer is dissolved. The beaker is then removed promptly from the hot plate and placed on a room temperature stirrer. While stirring, 20 ml of o-dichlorobenze is added and the mixture is allowed to cool to room temperature. Then, 2.5 ml of 20% LiCl in methanol is added. The mixture is titrated to a potentiometric end point with either 0.1N or 0.05N NaOH in benzyl alcohol using a Beckman combination electrode. The titration is done in monotonic mode adding 30 microliters every 20 seconds. A blank is also run, omitting only the sample. The acid endgroup content is calculated as follows:

$$COOH\ content = \frac{[(ml\ sample - ml\ blank) \times normality\ NaOH \times 1000]}{g\ sample}$$

The esterification step may be accomplished by numerous processes known in the art. See, for example, U.S. Pat. No. 3,506,622 to Higgins.

2. Diol-Incorporation Reaction Stage

In a subsequent stage of the process, the esterified material is continuously fed to a diol-incorporation reactor. Diol is also continuously fed to the diol-incorporation reactor at a flow rate less than about 15% of the flowrate of the esterified material. The pressure in the diol-incorporation reactor should be sufficient to minimize flashing of the diol, generally at least about 24.7 psia to 189.7 psia (170 kPa to 1310 kPa).

The purpose of the diol-incorporation reactor is to maintain temperature and pressure for a minimum period of time in order to increase the hydroxyl ends (on polymer chains as opposed to hydroxy ends on diol) relative to the carboxyl ends. The residence time in the diol-incorporation reactor should be at least about 15 seconds, and certainly not longer than about 15 minutes since the extent of degradation will increase with time. The reaction product from the diol-incorporation reactor typically has a lower DP than the esterified material, generally in the range of about 2 to about 7, and a reduced carboxyl content of about 25 to about 300 meq/kg lower than the esterified material entering the diol-incorporation reactor.

In addition to reacting diol with the esterified material, the diol-incorporation reactor serves to reduce the vinyl end group concentration in some oligomers such as PET by allowing water to hydrolyze the vinyl ends. This is a beneficial feature, since vinyl ends are a potential precursor to undesirable byproducts such as acetaldehyde in the case of PET.

Reactors that are suitable diol-incorporation reactors include continuously stirred tank reactors (CSTR), static mixers, or tubular reactors, such as a pipeline, or any reactor that will provide sufficient residence time. A pipeline reactor is preferred, for economic reasons, including heat transfer efficiency. A preferred embodiment of a pipeline reactor is disclosed in coassigned copending U.S. application Ser. No. 08/376,596 filed Jan. 20, 1995, hereby incorporated by reference in its entirety.

Subsequent to reaction in the diol-incorporation reactor, the reaction product is then preferably passed through a heated, pressure-reducing device to flash volatile condensation and esterification products. Volatile condensation and esterification products include water and diol. The pressure-reducing device may take various forms, for example it may be a static mixer, a shell-and-tube heat exchanger, or as in the preferred embodiment, a shell-and-tube heat exchanger, optionally preceded by a valve. The requirements of the heated, pressure-reducing device are only that sufficient heat and sufficiently low pressure are provided to allow flashing of the diol and other volatile condensation products.

The purpose of the pressure-reducing device is as follows. The diol-incorporation reactor needs to run under pressure to minimize flashing of the diol so that it will react with the esterified product. On the other hand, the column reactor (described next) runs more efficiently at atmospheric pressure. The pressure-reducing device, therefore, is a means for separating the two different pressures. The flashing takes heat away from the liquid, and it is more efficient to allow this flashing and concomitant reaction to occur before the column reactor, because the heat load on the column reactor and the required residence time in the column reactor is thereby reduced.

3. Column-Reactor Stage

Direct esterification of acid end groups and unreacted diacid with diol and hydroxyl endgroups, and polycondensation, are efficiently and rapidly accomplished using a column-reactor system that is operated continuously and countercurrently. Since the column reactor system is preferably operated at about atmospheric pressure (including slightly above or below atmospheric pressure), environmental contamination associated with a vacuum source can be avoided.

In a preferred embodiment of the invention, the reaction product from the pressure-reducing device is passed to a top part of a heated countercurrent column reactor. The column is typically heated to a temperature of at least 5° C. above the freezing point of the resulting prepolymer recovered from the bottom of the countercurrent column reactor by known methods such as jacketing or tracing.

The column reactor contains about 2 to 50 plates, preferably between 3 and 25 plates. While feeding the reaction product, a stream of predominantly inert gas is fed to the bottom of the column reactor. The predominantly inert gas stream flows upward through the column, carrying volatiles with it. The gas flow also creates surface area for mass transfer from the liquid phase to the vapor phase. By the phrase "predominantly inert gas" is meant that the gas stream fed to the reactor comprises greater than 50% by weight gas that is inert to the polycondensation reactions (such as $CO_2$, Ar, low-molecular-weight alkanes such as methane, nitrogen, and/or natural gas). Nitrogen is preferred. The gas stream may also include additional components such as polymer modifiers, water, or diol. The inert gas is suitably heated to a temperature of at least 5° C. above the freezing point of the resulting prepolymer recovered from the bottom of the countercurrent column reactor prior to feeding it into the column. The freezing point $T_c$ is defined in ASTM D 3418-82, where it is referred to as the "peak crystallization temperature".

In the column reactor, the reaction product continuously flows across multiple reactor plates and through the heated column reactor. At the same time, inert gas flows upward through the column reactor. The flowrate of the reaction product is such that the reaction product has a residence time in the reactor of at least about 2 minutes, preferably at least about 3 minutes.

The column reactor may comprise plates of any suitable kind known in the art, so long as they provide sufficient contact between the liquid and the gas. Plates that are suitable include sieve plates, bubble-cap plates, valve plates, and slot plates. Sieve plates are preferred because they are economical and less sensitive to suspended solids.

The inert gas is suitably fed into the column reactor at a flowrate of about 0.02 to about 0.75 kg inert gas/kg bottoms product exiting the column. Preferably, the flowrate is about 0.04 to about 0.3 kg gas/kg bottoms product. The range of acceptable flowrates will depend partly on column design. If the flowrate is too low, the liquid in the column will "weep" through the holes in the plates of the column. If the flow rate is too high, entrainment flooding may occur. A short, larger diameter column with few trays would have a higher optimal gas flow than a tall, smaller diameter column. Preferably, the liquid depth on the top tray is less than about 0.05 meters, which minimizes entrainment of liquid in the gas leaving the top tray of the reactor. By way of definition, "liquid depth" means the weir height of the tray plus the height of the crest over the weir in equivalent clear liquid.

It is optional to introduce additional diols, diacids or mixtures thereof, as well as their reaction products, to the esterifier and/or to the column reactor below the top tray. In the column reactor, this would provide for mixing-in of comonomers and modifiers. As another option, diol could be added as a vapor to contribute heat to the column. A polymer modifier, such as DEG, may also be added to the column below the top plate. A catalyst, such as but not limited to a polycondensation catalyst, may be added to the column reactor through a side stream, although this is not required. If in powder form, the catalyst may be dissolved in a liquid or prepared as a slurry prior to injecting it into the column reactor. Alternately, a side stream can be withdrawn from the column, the catalyst mixed in, and the side stream returned to the column.

Polyester prepolymer is collected from the bottom of the column reactor. The prepolymer has fewer acid end-groups, that is, lower carboxyl content than the material from the esterification reactor. Typically, the prepolymer collected will have a carboxyl content in the range of about 25 to about 800 meq/kg lower than the esterified material, and a degree of polymerization in the range of about 10 to about 30.

Another aspect of the invention involves removing water, diol, low-molecular-weight solids and degradation products from the inert gas exiting the top of the column reactor. This may be accomplished by various methods described more fully below. Optimally, the diol and low-molecular-weight solids recovered from the gas stream are recycled, after optional purification by methods known in the art, to the esterification reactor. The purified inert-gas stream is preferably passed through a compressor, a heat exchanger, a cooler to cool the discharge from the compressor and an absorber to reduce the concentration of low boiling compounds in the gas and passes again into the bottom part of the column reactor.

A continuous, countercurrent, column-reactor system, and the process by which polyester prepolymer is prepared from the reaction mass of the prior esterification stage, is most easily understood by reference to FIG. 1.

FIG. 1 is a schematic diagram of one embodiment of a process according to the present invention. This process begins with esterified material 33 from an esterification reactor 34 being fed to a tubular pipeline serving as a diol-incorporation reactor 10. Diol is added in line 31 just prior to the diol-incorporation reactor 10. The product of this reactor, in line 35, is then fed to a heated, pressure-reducing device 12 and from there into the top part of a countercurrent column reactor 14. Inert gas is fed via line 61 into a bottom portion of the countercurrent column reactor 14. PET prepolymer is collected via line 41.

The gas stream 39 from the countercurrent column reactor is continuously fed to a distillation column 16 equipped with a condenser 18. A bottoms product 43 comprising diol, water, dissolved low-molecular-weight solids and degradation products is collected from the distillation column and is passed to the prior esterification reactor 34 for reuse. The bottom products 43 may be further purified by methods known in the art to remove one or more of water, undesirable low boiling products, and solids prior to recycling to the esterification stage.

The vapor product 44 is fed to the aforementioned condenser 18 and a portion of the liquid product 47 from the condenser, comprising essentially water, is continuously passed to a waste water treatment system, with the remainder going back to the column to serve as reflux. The vapor product 49 from the condenser is passed to a compressor 20 for further treatment downstream to remove undesirable low boiling side products, such as acetaldehyde, in absorber 24.

A diol-rich side stream 45 may be withdrawn from the side of the distillation column 16 for reuse in prior reaction stages. This side stream typically should be at least about 90% pure, preferably at least about 95% pure.

Alternatively (not shown in FIG. 1), diol may be recovered from the inert gas stream 39 by means of an absorber column. In this embodiment, virgin diol (i.e., diol that has not previously been used, preferably at least 98% pure, most preferably at least 99% pure with less than about 0.1% water) is continuously fed into the top part of the absorber. A bottoms product is removed that comprises diol, water, dissolved low-molecular-weight solids and degradation products and can be passed to a prior esterification stage for reuse. The vapor product from the absorber column, comprising essentially inert gas, is continuously fed to a compressor for further treatment downstream to remove undesirable low boiling side products.

Returning to FIG. 1, the vapor product 49 from the condenser is, as previously mentioned, continuously fed to a compressor 20. Typically, this vapor product is pressurized to slightly above atmospheric pressure, about 5–10 psi (135–170 kPa) gauge. From the compressor, the vapor product, at a temperature of about typically within in the range of 50° to 90° C., is continuously fed via line 51 to a heat exchanger 22, which removes heat. Typically, a discharge temperature from the heat exchanger 22 of less than about 45° C. is preferred, more preferably less than about 35° C., and most preferably about 30° C. or lower temperature limited by the freezing point of water. The cooled vapor product in line 53 is then continuously fed upward through the absorber 24. Typically, the absorber is operated above atmospheric pressure. Virgin diol is continuously fed into the top part of the absorber via line 55 to absorb volatile by-products (e.g., acetaldehyde in the case of PET) as it flows downward through the absorber 24. The virgin diol is typically at a temperature less than about 40° C., and preferably less than about 35° C. Diols with freezing points above 40° C., for example, hexanediol, would be used at temperatures at least 5° C. above their freezing point. The vapor product in line 59 from the absorber comprises essentially inert gas with lower levels of low boiling compounds (for example about only 6 ppm by weight aldehyde in the process for making PET) is recycled back to the countercurrent column reactor 14 through line 61 and heat exchanger 26. Diol and dissolved volatile by-products are removed from the bottom of the absorber via line 57 and are passed back to the esterification reactor 34.

Other embodiments of the invention will be apparent to those skilled in the art based on the invention disclosed herein. It is intended that the specification and examples be considered as exemplary only, with the true scope and spirit of the invention being indicated by the claims.

EXAMPLE 1

About 6725 kg/hr of the esterification product of EG and TPA with a DP of 7.5 and an acidity of 714 meq/kg and a temperature of 275° C. is withdrawn from an esterifier and pumped through a pipe at a pressure of about 1000 kPa. About 306 kg/hr of ethylene glycol at about 170° C. is introduced into said pipe and is mixed with the product of the esterifier. The pipe is sized so that the mean residence time is about 71 seconds. Heat is applied to the pipe to maintain the pipe discharge temperature at about 273° C.

The pressure of the liquid in the pipe is reduced to about 150 kPa by flowing the liquid across a valve and into a heat exchanger. The volatile reaction products in the liquid are allowed to vaporize. The heat exchanger is designed so that the mean residence time of the liquid is about 50 seconds. The heat exchanger is controlled so that the discharge temperature of the liquid is about 280° C.

The discharge from the heat exchanger is fed to the top of a 0.75 meter diameter sieve plate column containing 13 trays. The outlet weirs on the trays are sized to provide 25 seconds mean liquid residence time on each tray. Heat is applied to the outside of the column to prevent heat loss and maintain the temperature of the reactor contents. About 445 kg/hr of gas, which is substantially nitrogen, at a temperature of 285° C. and a pressure of 120 kPa is fed to the bottom of the column.

Liquid prepolymer, at a flowrate of 6719 kg/hr, with a DP of 15 and an acidity of 100 meq/kg is withdrawn from the bottom of the column and is polymerized in the melt using methods known in the art or, alternatively, formed into particles, crystallized, and subsequently polymerized in the solid state. Alternatively, a recently developed method of particle formation is disclosed in commonly assigned, U.S. Pat. No. 5,510,454, issued on Apr. 23, 1996, which is hereby incorporated by reference.

About 757 kg/hr of gas is withdrawn from the top of the column. The gas consists of about 59% (by weight) nitrogen, about 25% ethylene glycol, about 12% water and lesser amounts of bis-hydroxyethyl-terephthalate, liquids entrained in the gas, and reaction by-products such as acetaldehyde and diethylene glycol. The gas is fed to the bottom of a distillation column fitted with a condenser. The distillation column may be packed or trayed. Different packings, such as Intalox® saddles, known in the art, can be used. The column typically contains a quantity of packing necessary to provide at least 4 theoretical plates and is about 0.4 meter in diameter. The condenser is operated so that the condensate is about 36° C. The reflux to the column is adjusted so that the temperature of the gas leaving the packing is about 80° C. About 184 kg/hr of bottom liquid product, containing ethylene glycol, suspended solids, and high-boiling reaction by-products, such as diethylene glycol, is removed from the bottom of the column. About 38 kg/hr of a side draw, containing principally ethylene glycol and water, is withdrawn from the column at a point where the vapor has traveled through about 25% of packing height. About 71 kg/hr of liquid condensate, which is substantially water, is withdrawn from the condenser and routed to a waste water treatment facility. About 463 kg/hr of vapor, which is about 96% nitrogen, about 3% water, 6200 ppm acetaldehyde and lesser amounts of low boiling reaction byproducts, is withdrawn from the condenser.

The vapor withdrawn from the condenser is compressed to 175 kPa using methods known in the art such as a rotary lobe blower. The gas leaving the compressor is cooled to 25° C. in a heat exchanger.

The gas leaving the heat exchanger is fed to the bottom of a packed absorber column. Virgin ethylene glycol (1980 kg/hr) is fed to the top of the absorber column. The packing in the column can be one of several types know in the art such as Intalox® saddles or Raschig rings. The liquid leaving the bottom of the absorber column is routed to the esterification stage. The gas from the top of the column, typically containing about 6 ppm by weight acetaldehyde, is reduced in pressure to about 120 kPa, heated to 285° C., and then fed to the bottom of the reactor column.

EXAMPLE 2

About 6705 kg/hr of the esterification product of EG and TPA with a DP of 6.5 and an acidity of 816 meq/kg and a temperature of 285° C. is withdrawn from an esterifier and pumped through a pipe at a pressure of about 1000 kPa. About 378 kg/hr of ethylene glycol at about 170° C. is introduced into said pipe and is mixed with the product of the esterifier. The pipe is sized so that the mean residence time is about 70 seconds. Heat is applied to the pipe to maintain the pipe discharge temperature at about 278° C.

The pressure of the liquid in the pipe is reduced to about 120 kPa by flowing the liquid across a valve and into a heat exchanger. The volatile reaction products in the liquid are allowed to vaporize. The heat exchanger is designed so that the mean residence time of the liquid is less than about 50 seconds. The heat exchanger is controlled so that the discharge temperature of the liquid is about 293° C.

The discharge from the heat exchanger is fed to the top of a 0.75 meter diameter sieve plate column containing 10 trays. The outlet weirs on the trays are sized to provide 16 seconds mean liquid residence time on the bottom nine (9) trays. The mean liquid residence time on the top tray is 8 seconds. Heat is applied to the outside of the column to prevent heat loss of the reactor contents. About 454 kg/hr of gas, which is substantially nitrogen, at a temperature of 285° C. and a pressure of 120 kPa is fed to the bottom of the column.

Liquid prepolymer, at a flowrate of 6627 kg/hr, with a DP of about 22 and an acidity of about 250 meq/kg is withdrawn from the bottom of the column and is polymerized in the melt using methods known in the art or, alternatively, formed into particles, crystallized, and subsequently polymerized in the solid state. Alternatively, a recently developed method of particle formation is disclosed in commonly assigned, U.S. Pat. No. 5,510,454, filed as U.S. patent application Ser. No. 08/376,600 on Jan. 20, 1995, hereby incorporated by reference.

About 910 kg/hr of gas is withdrawn from the top of the column. The gas consists of about 49.8% (by weight)

nitrogen, about 41.8% ethylene glycol, about 8% water and lesser amounts of bis-hydroxyethyl-terephthalate, liquids entrained in the gas, and reaction by-products such as acetaldehyde and diethylene glycol. The gas is fed to the bottom of a distillation column fitted with a condenser. The distillation column may be packed or trayed. Different packings, such as Intalox® saddles, known in the art, can be used. The column typically contains a quantity of packing or number of trays necessary to provide at least 5 theoretical plates and is about 0.4 meter in diameter. The condenser is operated so that the condensate is about 35° C. The reflux to the column is adjusted so that the temperature in the middle of the column is about 87° C. About 387 kg/hr of bottom liquid product, containing ethylene glycol, suspended solids, and high-boiling reaction by-products, such as diethylene glycol, is removed from the bottom of the column. About 52.4 kg/hr of liquid condensate, which is substantially water, is withdrawn from the condenser and routed to a waste water treatment facility. About 470 kg/hr of vapor, which is about 96.5% nitrogen, about 3.4% water, 660 ppm acetaldehyde and lesser amounts of low boiling reaction byproducts, is withdrawn from the condenser.

The vapor withdrawn from the condenser is compressed to 175 kPa using methods known in the art such as a rotary lobe blower. The gas leaving the compressor is cooled to 25° C. in a heat exchanger.

The gas leaving the heat exchanger is fed to the bottom of a packed absorber column. Virgin ethylene glycol (1980 kg/hr) is fed to the top of the absorber column. The packing in the column can be one of several types known in the art such as Intalox® saddles or Raschig rings. The liquid leaving the bottom of the absorber column is routed to the esterification stage. The gas from the top of the column, typically containing about 6 ppm, by weight, acetaldehyde, is reduced in pressure to about 120 kPa, heated to 285° C., and then fed to the bottom of the reactor column.

What is claimed is:

1. A continuous process for preparing polyester prepolymer comprising the steps of:

(a) esterifying a diacid, chosen from aliphatic or aromatic diacids having a molecular weight less than 300 with an diol, chosen from aliphatic and cycloaliphatic diols having a molecular weight less than 400, in an esterification reactor to form an esterified material having a carboxyl content of about 400 to about 1200 meq/kg and a degree of polymerization of about 2 to about 15;

(b) incorporating diol into the esterified material by continuously feeding the esterified material to a diol-incorporation reactor wherein the pressure ranges from about 24.7 psia to 189.7 psia (170 kPa to 1310 kPa) and the temperature ranges from about 200° C. to about 350° C. and wherein the diol is fed to the diol-incorporation reactor at a flowrate ranging from about 0.5% to about 15% of the flowrate of the esterified material, and allowing the diol and esterified material to react for at least 15 seconds in the diol-incorporation reactor to obtain a reaction product having a degree of polymerization ranging from about 2 to about 7 and a carboxyl content of about 25 to about 300 meq/kg lower than the esterified material entering the diol-incorporation reactor;

(c) continuously passing the reaction product through a heated, pressure-reducing device, thereby allowing diol and other volatile condensation products to flash off;

(d) continuously passing the reaction product into a top portion of a column reactor containing about 2 to about 50 plates, while countercurrently and continuously feeding into a bottom portion of the column reactor a stream of predominantly inert gas at a flowrate of about 0.02 to about 0.75 (kg inert gas)/(kg bottoms product), wherein the minimum temperature of the inert gas as it enters the column reactor is greater than about 5° C. above the freezing point of the prepolymer removed from the bottom of the column reactor and the flowrate of the reaction product is such that it has a residence time in the column reactor of at least about 2 minutes;

(e) withdrawing a gas stream from the top of the column reactor and removing water, diol, low-molecular-weight solids and degradation reaction products from the gas stream;

(f) collecting, from the bottom of the column reactor, polyester having a lower carboxyl content and a higher degree of polymerization than the esterified material from the esterification reaction, whereby the carboxyl content is in the range of about 25 to about 800 meq/kg lower than the esterified material entering the diol-incorporation reactor and the degree of polymerization is in the range of about 10 to about 30.

2. The process of claim 1 wherein the diacid is selected from the group consisting of terephthalic acid, isophthalic acid, adipic acid, succinic acid and naphthalenedicarboxylic acid.

3. The process of claim 1 wherein the diol is selected from the group consisting of ethanediol, propanediol, butanediol, and dimethylolcyclohexane.

4. The process of claim 1 further comprising:

(i) collecting the diol and low-molecular-weight solids recovered from the gas stream exiting top of the column reactor in step (e), and passing them to the esterification reactor for reuse; and (ii) passing the gas stream from step (e), in which the water, diol, low molecular weight solids and degradation reaction products have been removed, into a compressor, then into a heat exchanger, and finally into the bottom portion of the column reactor.

5. The process of claim 1 wherein the diol-incorporation reactor is selected from the group consisting of one or more tubular pipeline reactors, static mixers, a continuously stirred tank reactor, and combinations thereof.

6. The process of claim 1 wherein step (e) comprises:

(i) continuously passing the gas stream exiting the top of the column reactor into a distillation column equipped with a condenser;

(ii) removing a bottoms product from said distillation column, which bottoms product comprises diol, water, dissolved low-molecular-weight solids, and degradation products and then passing the bottoms product, optionally with intermediate purification, to the prior esterification reactor for reuse;

(iii) removing liquid product from the condenser, which liquid product comprises essentially water, and refluxing a portion of the liquid product back to the distillation column; and (iv) passing a vapor product from the condenser, comprising essentially inert gas, to a compressor, then into a heat exchanger, and finally into the bottom part of the counter current column reactor.

7. The process of claim 4 further comprising withdrawing a diol-rich side stream from the distillation column for reuse in the prior esterification reactor and/or the diol-incorporation reactor.

8. The process of claim 1 wherein step (e) comprises:
(i) continuously passing the gas stream exiting the top of the countercurrent column reactor into an absorber column;
(ii) continuously feeding virgin diol into the top part of the absorber;
(iii) removing a bottoms product, comprising diol, water, dissolved low molecular weight solids, and degradation products, and passing it to the prior esterification stage for reuse;
(iv) passing a vapor product from the absorber column, comprising essentially inert gas, to a compressor, then into a heat exchanger, and finally into the bottom portion of the column reactor.

9. The process of claim 4, claim 5 or claim 6 further comprising removing volatile by-products from the gas stream exiting the compressor, by means of the following steps:
(i) continuously passing the gas stream from the compressor, through a cooler, upward through an absorber, and out the top portion of the absorber;
(ii) continuously passing the gas stream from the top of the absorber and, after heating the gas stream, passing it to the bottom of the column reactor for reuse;
(iii) continuously feeding virgin diol into the top part of the absorber to absorb dissolved volatile by-products;
(iv) removing diol and dissolved volatile by-products from the bottom of the absorber and passing them to the esterification reactor.

10. The process of claim 9 wherein the temperature of the inert gas exiting the cooler is less than about 45° C., and the temperature of the virgin diol fed to the absorber is less than about 40° C. for diols with freezing points below 40° C.

11. The process of claim 1 or claim 2 or claim 3 or claim 4 or claim 5 or claim 6 or claim 7 or claim 8 furthering comprising adding in step (a), (b), and/or (c) up to 10% of a diol selected from the group consisting of butanediol isomers, propanediol isomers, diethylene glycol, cyclohexane dimethanol, polyethylene glycols, and mixtures thereof, and wherein the temperature of the inert gas fed to the bottom of the column is at least 5° C. above the freezing point of the resulting prepolymer.

12. The process of claim 1 or claim 2 or claim 3 or claim 4 or claim 5 or claim 6 or claim 7 or claim 8 further comprising adding in step (a), (b), and/or (c) up to 10% by weight of one or more polyols having three or more hydroxyl groups and/or one or more acid or anhydride branching agents, in order to modify the properties of the final product.

13. The process of claim 1 or claim 2 or claim 3 or claim 4 or claim 5 or claim 6 or claim 7 or claim 8 further comprising adding in step (a), (b), and/or (c) up to 10% by weight of a diacid selected from the group consisting of isophthalic acid, 2,6 napthalenedicarboxylic acid, cyclohexane dicarboxylic acid, azelaic acid, glutaric acid, or mixtures thereof, and further wherein the temperature of the inert gas fed to the bottom of the column is at least 5° C. above the freezing point of the resulting prepolymer.

14. The process of claim 1 or claim 2 or claim 3 or claim 4 or claim 5 or claim 6 or claim 7 or claim 8 further comprising adding in step (a) up to 10% by weight of a diacid selected from the group consisting of alkyl dicarboxylic acids containing from 4 to 38 carbon atoms, aryl dicarboxylic acids containing from 8 to 20 carbon atoms, and mixtures thereof, and further wherein the temperature of the inert gas fed to the bottom of the column is at least 5° C. above the freezing point of the resulting prepolymer.

15. The processes of claim 1 or claim 2 or claim 3 or claim 4 or claim 5 or claim 6 or claim 7 or claim 8 wherein the gas fed to the bottom of the column reactor is fed at a flowrate ranging from about 0.02 to about 0.75 (kg gas)/(kg bottoms product) from the bottom of the column reactor.

16. The process of claim 1 or claim 4 wherein the plates in the column reactor are selected from the group consisting of sieve plates, slot plates, bubble cap plates, valve cap plates, and combinations thereof.

17. The process of claim 1 or claim 4 wherein the column reactor has between 3 and 25 plates.

18. The process of claim 1 or claim 4 wherein one or more diols, diacids, or mixtures thereof, and their reaction products, are added to the column reactor below the top plate.

19. The process of claim 1 or claim 4 comprising adding one or more polymer modifiers below the top plate of the column.

20. The process of claim 19 wherein the modifier is diethylene glycol.

21. The process of claim 1 or claim 4 wherein one or more catalysts are used to aid esterification, diol incorporation, or polycondensation.

22. The process of claim 1 or claim 4 wherein the liquid depth on the top tray is less than about 0.05 meters.

23. The process of claim 1 wherein the prepolymer prepared is poly(ethylene terephthalate), the diacid is terephthalic acid and the diol is ethylene glycol.

* * * * *